United States Patent [19]

Noel

[11] Patent Number: 5,401,773

[45] Date of Patent: Mar. 28, 1995

[54] LACTIC ACID ACYLATES

[75] Inventor: Hugues Noel, Ermont, France

[73] Assignee: Roussel-Uclaf, France

[21] Appl. No.: 651,466

[22] Filed: Feb. 6, 1991

[30] Foreign Application Priority Data

Feb. 22, 1990 [FR] France ................................ 90 02176

[51] Int. Cl.$^6$ ............................................ A61K 31/225
[52] U.S. Cl. .................... 514/547; 554/223;
554/227; 554/549; 554/552; 554/886; 554/887
[58] Field of Search .................... 260/410.6; 554/223,
554/227; 514/547, 549, 552, 886, 887

[56] References Cited

U.S. PATENT DOCUMENTS 4,846,991  7/1989  Suzere et al. .................... 260/410.6

OTHER PUBLICATIONS

Chemical Abstracts, Raiser et al, vol. 86, #7, p. , 1976, 43202k.

Chemical Abstracts, vol. 73, #22, p. , 1969 112980h, abstract of FR 2,003,312.

*Primary Examiner*—José G. Dees
*Assistant Examiner*—Deborah D. Carr
*Attorney, Agent, or Firm*—Bierman and Muserlian

[57] ABSTRACT

All possible isomeric forms, racemic mixtures and enantiomeric and diastereoisomeric forms of a compound selected from the group consisting of a compound of the formula

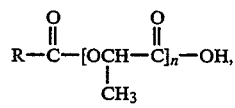

wherein R is alkenyl of 10 carbon atoms, n is an integer from 1 to 3 and their non-toxic salts useful for treating comedones.

9 Claims, No Drawings

LACTIC ACID ACYLATES

STATE OF THE ART

Related literature includes U.S. Pat. No. 3,933,825, French Patent No. 2,183,070 and German Patent No. 2,456,631.

OBJECTS OF THE INVENTION

It is an object of the invention to provide the novel compounds of formula I and their salts and a novel process for their preparation.

It is another object of the invention to provide novel compositions and a method for treating comedones in warm-blooded animals.

These and other objects and advantages of the invention will become obvious from the following detailed description.

THE INVENTION

The novel compositions of the invention are all possible isomeric forms, racemic mixtures and etantiomeric and diastereoisomeric forms of a compound selected from the group consisting of a compound of the formula

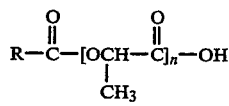

wherein R is alkenyl of 10 carbon atoms, n is an integer from 1 to 3 and their non-toxic salts.

In R which is a decenyl, the double bond may be situated anywhere in the chain. Examples of suitable decenyls are 8-decenyl, 7-decenyl or 6-decenyl radical, but preferably R is 9-decenyl, the figures indicate the position of the first of the two carbon atoms which carry the double bond, the carbon atoms being counted starting from the carbon atom linked to the —CO—.

The salts of the products of formula I, as defined above which can be mentioned are metal salts such as aluminium, copper, magnesium or zinc, but also sodium, potassium, triethanolamine or even dimethylaminoethanol salts. Preferred are lactylates of zinc, sodium or potassium.

The preferred products of formula I are those wherein R is 9-decenyl of the formula $CH_2=CH(CH_2)_8-$ and n is 1 or 2, as well as their salts, in all the possible isomer forms, racemic, enantiomeric or diastereoisomeric. Such lactic acid acylates therefore correspond to 10-undecenoyl 1-lactylic acid when n is equal to 1 and to 10-undecenoyl 2-lactylic acid when n is equal to 2. Especially preferred is 10-undecenoyl 1-lactylic acid as well as its salts, in all the possible isomer forms, racemic, enantiomeric and diastereoisomeric.

The process of the invention for the preparation of the compounds of formula I comprises reacting an equivalent of a product of the formula

     II wherein R is alkenyl of 10 carbon atoms with about 1 to 3 equivalents of lactic acid:

in racemic or optically active form and, optionally the product of formula I is treated with a mineral or organic base to obtain the corresponding salt and the racemic products of formula I may be separated into their enantiomers or diastereoisomers.

The product of formula II is an undecylenic acid and the acylation reaction of the product of formula II with lactic acid can be obtained by direct contact without a solvent in the presence of a catalyst such as p-toluene sulfonic acid.

The products in which n varies from 1 to 3 can be obtained by using a variable relative proportion of the product of formula II and of lactic acid in the presence of each other. Thus, one mole of product of formula II is used for n moles of lactic acid according to the product of formula I to be obtained.

The treatment of the products of formula I with a mineral or organic base to obtain the corresponding salt, as well as the separation of the racemic products of formula I into their enantiomers or diastereoisomers, can be carried out by the standard methods known to a man skilled in the art.

The novel comedolytic compositions of the invention are comprised of a comedolytically effective amount of at least one compound of formula I or its salts and a cosmetic or pharmaceutical carrier. The compositions may be in the form of foams or aerosols, pressed powders, solutions, emulsions, creams, ointments, powders, milks, cosmetic milks, aqueous or anhydrous gels, lotions, antipellicular lotions, shampoos or bubble baths. Such forms may be packaged in pots or tubes, in glass or plastic jars or optionally in dropping bottles or also in ampoules.

Examples of excipients are hydrocarbons, silicone oils, synthetic triglycerides, vegetable, animal or mineral waxes, fatty acids and alcohols, esters of fatty acids or of a fatty alcohol, amides of fatty acids, nonionic surface-active agents, anionic surface-active agents, natural or synthetic jellifying polysaccharides, deacetylated chitin, cellulose derivatives, guar derivatives, polyols, polyalkylene glycols, mineral fillers, organic pigments or organic coloring laquers as well as other excipients known and currently used such as, for example, carboxyvinyl type polymers, polyethylene glycols, propylene glycol, fatty acid triglycerides, stearyl derivatives such as glycerol stearate, alcohols such as stearyl alcohols, keto stearyl alcohols, ketyl alcohol, polyoxy ethylene ketyl ether, vegetable oils such as soft almond oil, mineral oils such as vaseline oil, glycerine, lanolin derivatives, talc, wetting, thickening and stabilizing agents, emulsifiers, preservatives, perfumes and colorants.

The cosmetic compositions can be presented as standard skincare products, for example in the form of moisturizing creams, total filter creams, day creams, night creams, masks, or as make-up products, for example, foundation and tinting cream, or as make-up removing products or also as health products. The same excipients as those indicated above for the preparation of pharmaceutical compositions and which are the usual excipients of the pharmaceutical and cosmetic industry can be used in the preparation of such cosmetic compositions.

Active ingredients normally used in skin-care products can also be included in the preparation of such cosmetic compositions: among these ordinary active ingredients there can be mentioned, for example, moisturizing agents such as glycerin, amino acid salts, sorbitol, glycol, polyethylene glycol, sun filters, dihydroxyacetone, zinc oxide, anti-pellicular agents such as piroctone olamine, ethanolamides of undecylenic acid, acylates of hydrolyzed proteins, including abietate (salt of abietic acid which is a terpenic acid from resinuous wood) and undecylenate, fungicide and bactericide preservatives such as those listed, for example, in annex 6 of the European Directive 76 768 EEC, benzoyl peroxide, plant extracts, extracts from animal organs, sera.

The compositions have a significant comedolytic activity. Comedones are formed in the pilosebaceous follioles following abnormalities of keratinization and desquamation leading to an accumulation of keratinized material which forms a plug. Common acne and regular use of cosmetic products which are unsuitable or which contain comedogenic substances are frequent causes of the appearance of comedones. The use of substances of keratolytic and sebosuppressive effect has been known for a long time in the treatment of comedones, notably acid vitamin A for treating acne, azelaic acid or also 13-cis-retinoic acid. Lactic acid acylates have the advantage of being, in particular, much more stable than acid vitamin A, and are, furthermore, very well tolerated.

Due to their very useful comedolytic properties illustrated hereafter, the pharmaceutical compositions can be used in the treatment of skin suffering from acne, greasy or seborrheic skin and skin which has reacted to the use of comedogenic substances.

The novel method of the invention of treating comedones comprises topically applying to the skin of warm-blooded animals a comedolytically effective amount of at least one compound of formula I or its salts. Preferably, the compositions are applied at a dosage between 0.1 and 75% and preferably between 5% and 25% of 10-undecenoyl 1-lactylic acid or one of its salts. The compositions should be endowed with a great affinity for the skin, be perfectly well tolerated, stable, have an adequate consistency allowing an easy and agreeable use.

The starting products used of formula II as defined above and lactic acid are commercially-available products,,in particular the products of formula II are sold by the company ATOCHEM.

In the following examples, there are described several preferred embodiments to illustrate the invention. However, it should be understood that the invention is not intended to be limited to the specific embodiments.

EXAMPLE 1

10-UNDECENOYL 2-LACTYLIC ACID 400 g of 90% lactic acid and 368.5 g of 10-undecylenic acid were mixed together, under reduced pressure and the reaction was carried out in the presence of p-toluene sulfonic acid with heating for about 10 hours at a temperature of about 150° C. to obtain 674.5 g of undecenoyl lactylic acids, the mixture being mainly constituted by 10-undecenoyl 2-lactylic acid.

EXAMPLE 2

10-Undecenoyl 1-Lactylic Acid 32.8 g of the product of Example 1, 200 ml of distilled water and 8 g of sodium hydroxide were mixed together and the mixture was maintained for about three weeks at a temperature of about 25° C., the pH stabilizing at 6.9. After addition of hydrochloric acid until a pH of i was reached, extraction was carried out with about 100 ml of chloroform. The solvent was evaporated off to obtain the expected product.

EXAMPLE 3

Zinc 10-Undecenoyl 2-Lactylate 32.8 g of the product of Example 1 and 4 g of zinc oxide were ground for about 3 consecutive days and then dried in a dessicator over anhydrous silica. After about a week, a homogenous paste was obtained.

EXAMPLE 4

Zinc 10-Undecenoyl 1-Lactylate 120 ml of a 1N aqueous solution of zinc sulfate was added to the solution of the product of Example 2, obtained after stabilization of the pH at 6.9. The oily precipitate formed was washed four times with about 50 ml of distilled water, then dried by the procedure of Example 3.

EXAMPLE 5

Foundation Cream

| | |
|---|---|
| Pentaerythritol monostearate | 6.5 |
| Glycerol monoundecylenate | 1.0 |
| Sitosterol | 0.8 |
| Sorbitan monostearate | 1.0 |
| Macadamia oil | 1.2 |
| Oenothera oil | 2.0 |
| Perhydrosqualene | 0.5 |
| Stearyl dimethyl siloxane | 2.0 |
| Cyclosiloxane | 5.0 |
| Lauryl benzoate | 5.0 |
| Ethoxylated nonylphenol | 1.0 |
| Ethoxylated stearic acid | 2.2 |
| Abietate of hydrolyzed proteins and potassium | 3.0 |
| Zinc oxide | 3.0 |
| Zinc 10-undecenoyl 1-lactylate | 7.0 |
| Titanium oxide | 3.5 |
| Talc | 2.0 |
| Silica | 1.0 |
| Iron oxide | 3.0 |
| 1,3-butanediol | 5.0 |
| Preservative | 0.3 |
| Perfume | 0.2 |
| Demineralized water s.q. for | 100 |

EXAMPLE 6

Moisturizing Cream

| | |
|---|---|
| Sitosterol | 1.0 |
| Macadamia oil | 3.0 |
| Ethyl hexyl laurate myristate | 9.0 |
| Ketyl alcohol | 0.7 |
| Decamethyl cyclopentasiloxane | 6.0 |
| Ethylhexyl paramethoxycinnamate | 2.0 |
| Gamma orizanol | 0.5 |
| Isohexadecane | 12.0 |
| Pentaerythritol monostearate | 8.0 |
| Glucosamine hydrochloride | 0.2 |
| Lactic acid | 0.5 |
| Sodium pyrolidone carboxylate | 0.5 |
| Sodium 10-undecenoyl 1-lactylate | 7.0 |
| Glycerine | 2.0 |
| Preservative | 0.3 |
| Perfume | 0.3 |
| Demineralized water s.q. for | 100 |

EXAMPLE 7

Washing Milk

| | |
|---|---|
| Citric acid | 0.5 |
| Ethoxylated stearic acid | 2.5 |
| Glycerol monostearate | 2.5 |
| Polysorbate 60 | 2.0 |
| Monoglyceride lactate | 2.6 |
| Propanediol caprate caprylate | 2.4 |
| Ethylhexyl palmitate | 8.0 |
| Sorbitan oleate | 2.0 |
| Sorbitan monostearate | 1.0 |
| St-Johns-Wort extract | 3.0 |
| Elder water | 4.0 |
| Perfume | 0.3 |
| Preservative | 0.3 |
| Sodium 10-undecenoyl 1-lactylate | 3.0 |
| Demineralized water s.q. for | 100 |

EXAMPLE 8

Anti-pellicular Lotion

| | |
|---|---|
| Potassium 10-undecenoyl 1-lacylate | 1.0 |
| Ethoxylated lauric alcohol | 1.0 |
| Ethoxylated octyl-2-dodecylic alcohol | 0.9 |
| Undecylenic acid monoethanolamide | 0.5 |
| OCTOPIROX ® | 0.4 |
| Carbomer 940 | 0.15 |
| Citric acid | 0.10 |
| Preservative | 0.30 |
| Perfume | 0.10 |
| Demineralized water s.q. for | 100 |

EXAMPLE 9

Total Filter

| | |
|---|---|
| Hectorite | 1.0 |
| 1,3-butanediol | 3.0 |
| Marie thistle extract | 3.0 |
| Phenylbenzimidazol sulfonic acid | 2.0 |
| 50% L lysine | 2.2 |
| Zinc 10-undecenoyl 1-lactylate | 10.0 |
| Propylene glycol monostearate | 1.8 |
| Stearic acid | 3.0 |
| Sitosterol | 2.0 |
| Sodium stearoyl N methyl taurate | 1.0 |
| Oenothera oil | 1.5 |
| Karite butter | 2.0 |
| Hybrid saffron oil | 1.0 |
| Glycerol tripalmitate stearate | 8.0 |
| Hydrogenated copra oil | 5.0 |
| Cyclosiloxane | 2.0 |
| Phenylmethylsiloxane | 1.0 |
| Ethylhexyl paramethoxycinnamate | 7.5 |
| Methoxy butyl dibenzoyl methane | 2.0 |
| DL alpha-tocopherol | 0.1 |
| Preservative | 0.3 |
| Perfume | 0.3 |
| Demineralized water s.q. for | 100 |

Test for Comedolytic Activity of the Product of Example 6

The animal chosen for the test for comedolytic activity was the Hairless Rhino mouse (hr rh), female sex, this choice being due to the fact that the skin of such an animal has a large density of comedones of a large diameter and narrow orifice. The application of the comedolytic agents on the animal's skin causes the comedo's orifice to open, and the horny material and sebum that it contains to be released. Two groups were made up, each group containing 6 mice which were 6 weeks old at the start of the test and weighing on average 18 g each. The first group was made up of mice treated with distilled water (negative control group), the second group was made up of mice treated with the product of Example 6, such a treatment consisting of a topical application of the product studied on the interscapular area at a dose of 0.02 ml, 5 days out of 7 over 21 days. The animals were killed at the end of the three weeks of treatment, 24 hours after the last application. Biopsies of the skin were then taken from the treated areas of the animals and from these biopsies, sections were prepared in readiness for a standard morphometric study carried out by methods known to a man skilled in the art.

The following parameters are measured:
diameter of the opening of the comedone

| at the surface | or d |
|---|---|
| diameter of the comedo | or D |
| profile of the comedo | or R = d/D |

The relationship R=d/D allows the action of the comedolytic agents to be quantified. The percentage of inhibition of the comedones was calculated for the product of Example 6 relative to the negative control, that is the following relationship:

$$\% \text{ inhibition} = \frac{(\text{product } R - \text{negative control } R) \times 100}{\text{negative control } R}$$

The result obtained is 121.9, thus showing the effectiveness of the product studied.

Various modifications of the products and methods of the invention may be made without departing from the spirit or scope thereof and it is to be understood that the invention is intended to be limited only as defined in the appended claims.

What is claimed is:

1. All possible isomeric forms, racemic mixtures and enantiomeric and diastereoismeric forms of a compound selected from the group consisting of a compound of the formula

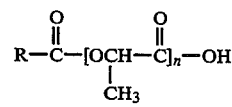

wherein R is alkenyl of 10 carbon atoms, n is an integer from 1 to 3 and their non-toxic salts.

2. A compound of claim 1 wherein n is 1 or 2 and R is $CH_2=CH-(CH_2)_8-$.

3. A compound of claim 1 which is 10-undecenoyl 1-lactylic acid and its salts.

4. A composition for treating comedones comprising a comedonically effective amount of at least one compound of claim 1 and a cosmetic or pharmaceutical carrier.

5. A composition of claim 4 wherein n is 1 or 2 and R is $CH_2=CH-(CH_2)_8-$.

6. A composition of claim 4 wherein the active ingredient is 10-undecenoyl 1-lactylic acid or its salts.

7. A method of treating comedones in warm-blooded animals comprising applying to the skin of warm-blooded animals a comedonically effective amount of at least one compound of claim 1.

8. A method of claim 7 wherein n is 1 or 2 and R is $CH_2=CH-(CH_2)_8-$.

9. A method of claim 7 wherein the active ingredient is -undecenoyl 1-lactylic acid or its salts.

* * * * *